United States Patent
Biju et al.

(10) Patent No.: US 11,058,369 B2
(45) Date of Patent: Jul. 13, 2021

(54) SYSTEMS AND METHODS FOR COHERENT SCATTER IMAGING USING A SEGMENTED PHOTON-COUNTING DETECTOR FOR COMPUTED TOMOGRAPHY

(71) Applicant: GE Precision Healthcare LLC, Milwaukee, WI (US)

(72) Inventors: Jacob Biju, Niskayuna, NY (US); Brian David Yanoff, Niskayuna, NY (US); Peter Edic, Albany, NY (US)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 68 days.

(21) Appl. No.: 16/686,037

(22) Filed: Nov. 15, 2019

(65) Prior Publication Data
US 2021/0145373 A1    May 20, 2021

(51) Int. Cl.
| | |
|---|---|
| A61B 6/03 | (2006.01) |
| A61B 6/00 | (2006.01) |
| G01N 23/201 | (2018.01) |
| G01T 1/24 | (2006.01) |
| G01T 1/29 | (2006.01) |

(52) U.S. Cl.
CPC ............ *A61B 6/032* (2013.01); *A61B 6/4241* (2013.01); *G01N 23/201* (2013.01); *G01T 1/242* (2013.01); *G01T 1/2985* (2013.01)

(58) Field of Classification Search
CPC ..... G01N 23/201; G01T 1/242; G01T 1/2985; A61B 6/032; A61B 6/4241
See application file for complete search history.

(56) References Cited

U.S. PATENT DOCUMENTS

| | | | |
|---|---|---|---|
| 5,905,809 A | 5/1999 | Timmer | |
| 6,442,233 B1 * | 8/2002 | Grodzins | G01V 5/0025 378/57 |
| 6,744,845 B2 | 6/2004 | Harding et al. | |
| 6,973,158 B2 | 12/2005 | Besson | |
| 7,477,725 B2 | 1/2009 | Harding | |
| 7,529,341 B2 | 5/2009 | Schlomka et al. | |
| 7,580,499 B2 | 8/2009 | Van Stevendaal et al. | |
| 7,590,215 B2 | 9/2009 | Schlomka | |
| 7,876,879 B2 | 1/2011 | Morton | |
| 8,121,249 B2 | 2/2012 | Wang et al. | |

(Continued)

FOREIGN PATENT DOCUMENTS

EP    1516588 A1    3/2005

*Primary Examiner* — Michael C Bryant
(74) *Attorney, Agent, or Firm* — McCoy Russell LLP

(57) ABSTRACT

Methods and systems are provided for coherent scattered imaging using a computed tomography system with segmented detector arrays. In one embodiment, a method includes imaging a region of interest with an x-ray source and a segmented photon-counting detector array, detecting a position of an object of interest in the region of interest, selectively scanning, via the x-ray source and the segmented photon-counting detector array, the object of interest, detecting a coherent scatter signal from the object of interest with the segmented photon-counting detector array, and determining a material of the object of interest based on the detected coherent scatter signal. In this way, the coherent scatter signal may be used to identify and investigate lesions or other objects of interest within an imaged volume.

20 Claims, 8 Drawing Sheets

(56) References Cited

U.S. PATENT DOCUMENTS

| | | |
|---|---|---|
| 9,335,281 B2 | 5/2016 | Marks et al. |
| 9,538,975 B2 | 1/2017 | Silver |
| 2006/0023832 A1 | 2/2006 | Edic et al. |
| 2007/0019782 A1 | 1/2007 | Van Stevendaal et al. |
| 2007/0140410 A1 | 6/2007 | Van Stevendaal et al. |
| 2007/0172026 A1 | 7/2007 | Schlomka et al. |
| 2007/0189444 A1 | 8/2007 | Van Steven-Daal et al. |
| 2008/0095305 A1 | 4/2008 | Ziegler et al. |
| 2008/0317311 A1 | 12/2008 | Grass et al. |
| 2009/0060124 A1 | 3/2009 | Grass et al. |
| 2009/0268862 A1 | 10/2009 | Ziegler |
| 2010/0061512 A1* | 3/2010 | Edie .................. G01N 23/20 378/71 |
| 2010/0135454 A1 | 6/2010 | Noo |
| 2010/0310037 A1 | 12/2010 | Wang et al. |
| 2011/0019797 A1 | 1/2011 | Morton |
| 2013/0032715 A1 | 2/2013 | Zhu et al. |
| 2016/0170075 A1* | 6/2016 | Schafer .............. G01N 23/2209 378/9 |
| 2020/0158896 A1* | 5/2020 | Danielsson ............. G01T 1/243 |

\* cited by examiner

SYSTEMS AND METHODS FOR COHERENT SCATTER IMAGING USING A SEGMENTED PHOTON-COUNTING DETECTOR FOR COMPUTED TOMOGRAPHY

FIELD

Embodiments of the subject matter disclosed herein relate to medical and industrial imaging systems, and more particularly, to coherent scatter imaging via a computed tomography (CT) imaging system comprising a segmented photon-counting detector.

BACKGROUND

Non-invasive imaging technologies allow images of the internal structures of a patient or object to be obtained without performing an invasive procedure on the patient or object. In particular, technologies such as computed tomography (CT) use various physical principles, such as the differential transmission of x-rays through the target volume, to acquire projection data and to construct tomographic images (e.g., three-dimensional representations of the interior of the human body or of other imaged structures).

BRIEF DESCRIPTION

In one embodiment, a method comprises imaging a region of interest with an x-ray source and a segmented photon-counting detector array, detecting a position of an object of interest in the region of interest, selectively scanning, via the x-ray source and the segmented photon-counting detector array, the object of interest, detecting a coherent scatter signal from the object of interest with the segmented photon-counting detector array, and determining a material comprising the object of interest based on the detected coherent scatter signal. In this way, the coherent scatter signal may be used to identify and characterize lesions or other objects of interest within an imaged volume.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure, and may be more generally applied to both medical imaging and non-destructive evaluation of inanimate objects.

BRIEF DESCRIPTION OF THE DRAWINGS

The present invention will be better understood from reading the following description of non-limiting embodiments, with reference to the attached drawings, wherein below.

DETAILED DESCRIPTION

Figure 3:
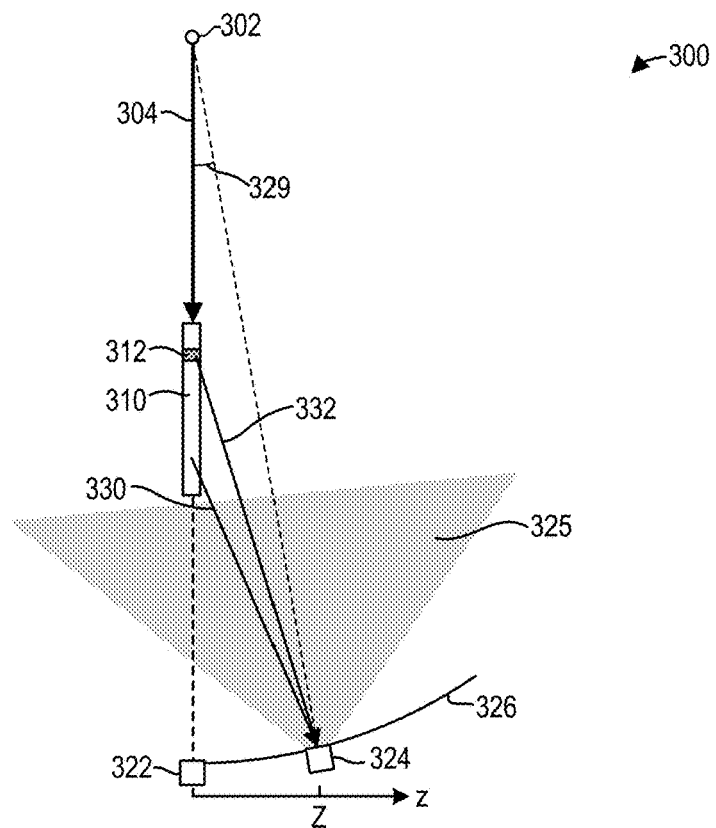
FIG. 3 shows a diagram illustrating coherent scatter imaging with non-segmented detectors, according to an embodiment.
Figure 4:
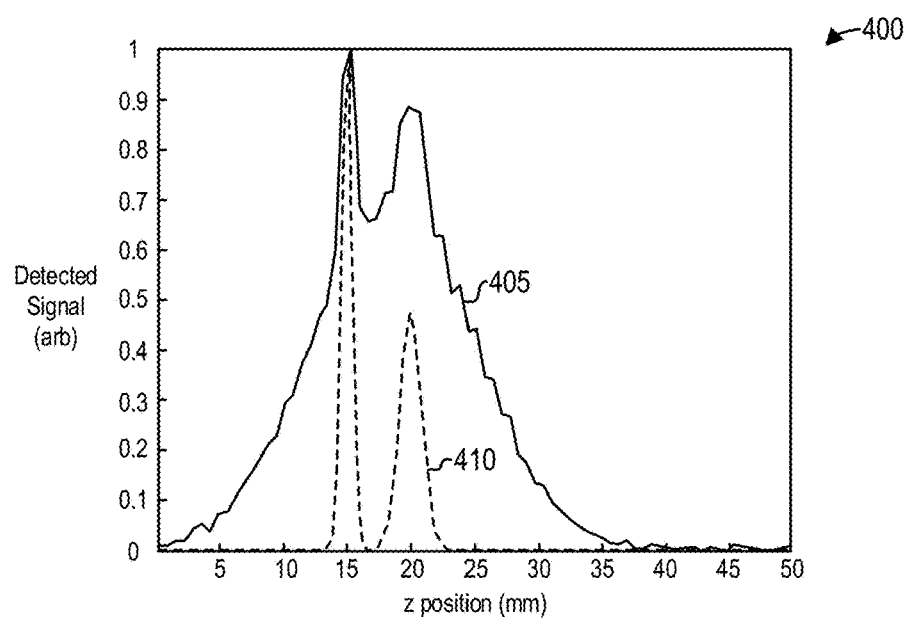
FIG. 4 shows a graph illustrating how a coherent scatter signal is dominated by background signals for non-segmented detectors, according to an embodiment.
Figure 5:
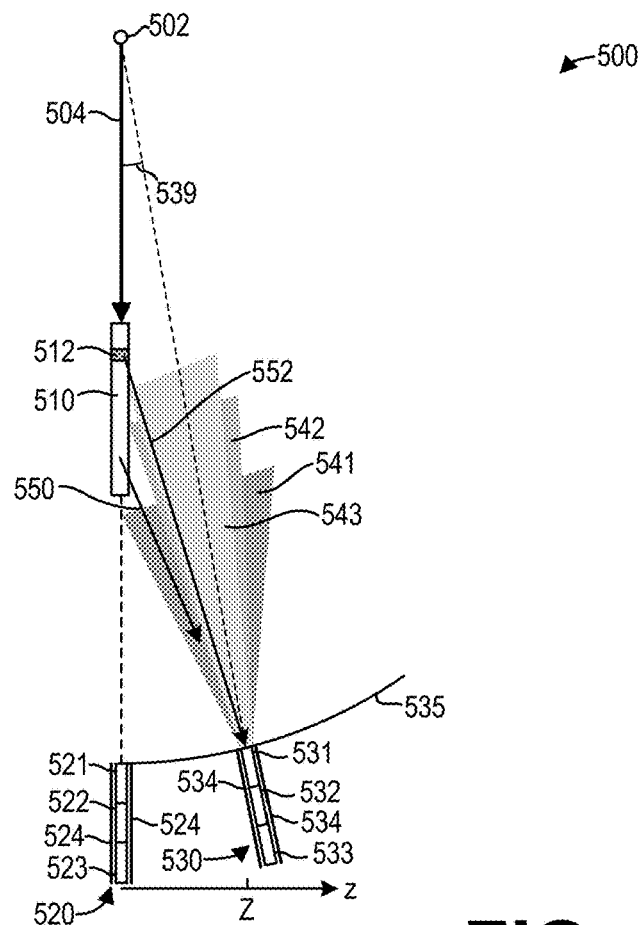
FIG. 5 shows a diagram illustrating coherent scatter imaging with segmented detectors, according to an exemplary embodiment.
Figure 6:
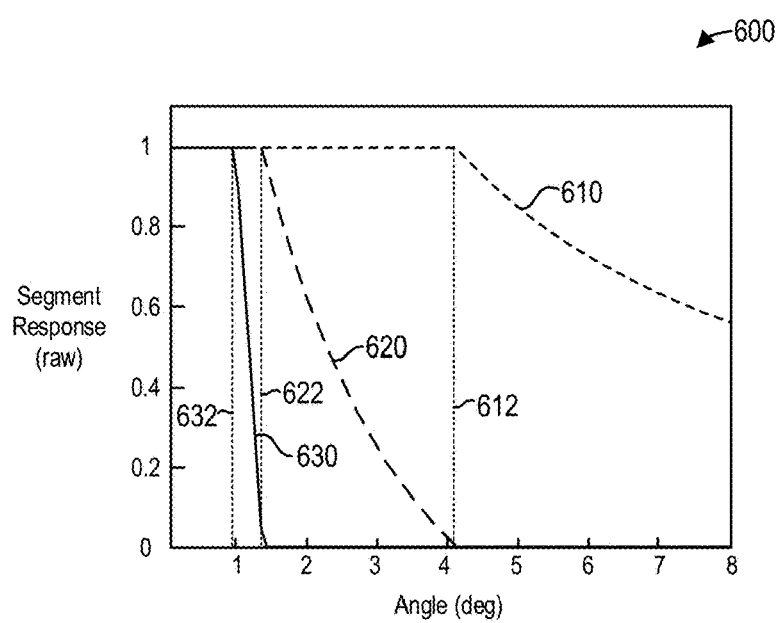
FIG. 6 shows a graph illustrating receptive fields of segments of a segmented detector, according to an exemplary embodiment.
Figure 7:
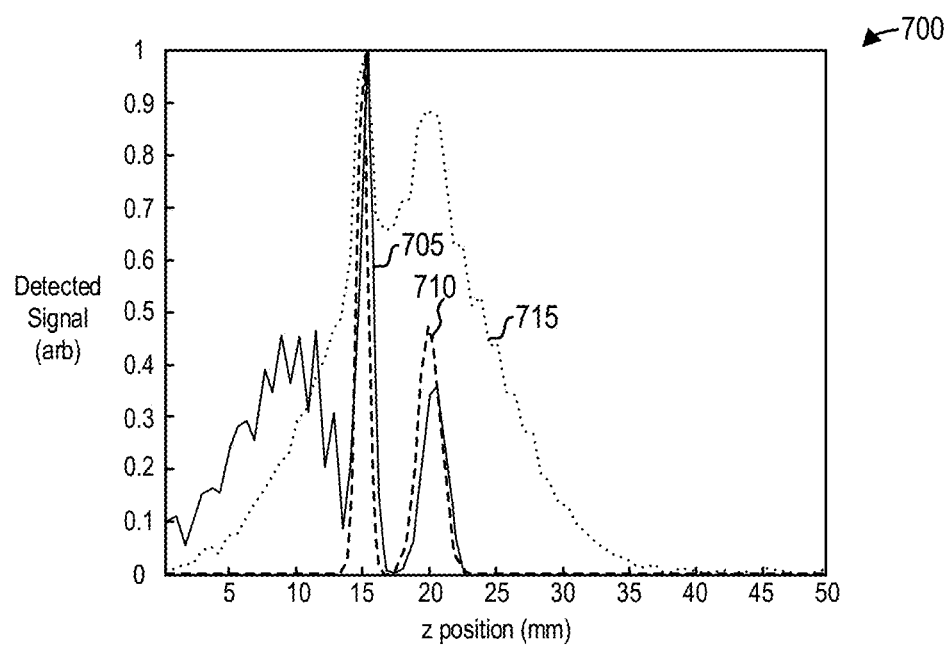
FIG. 7 shows a graph illustrating how a coherent scatter signal is detected with a segmented detector, according to an exemplary embodiment.
Figure 8:
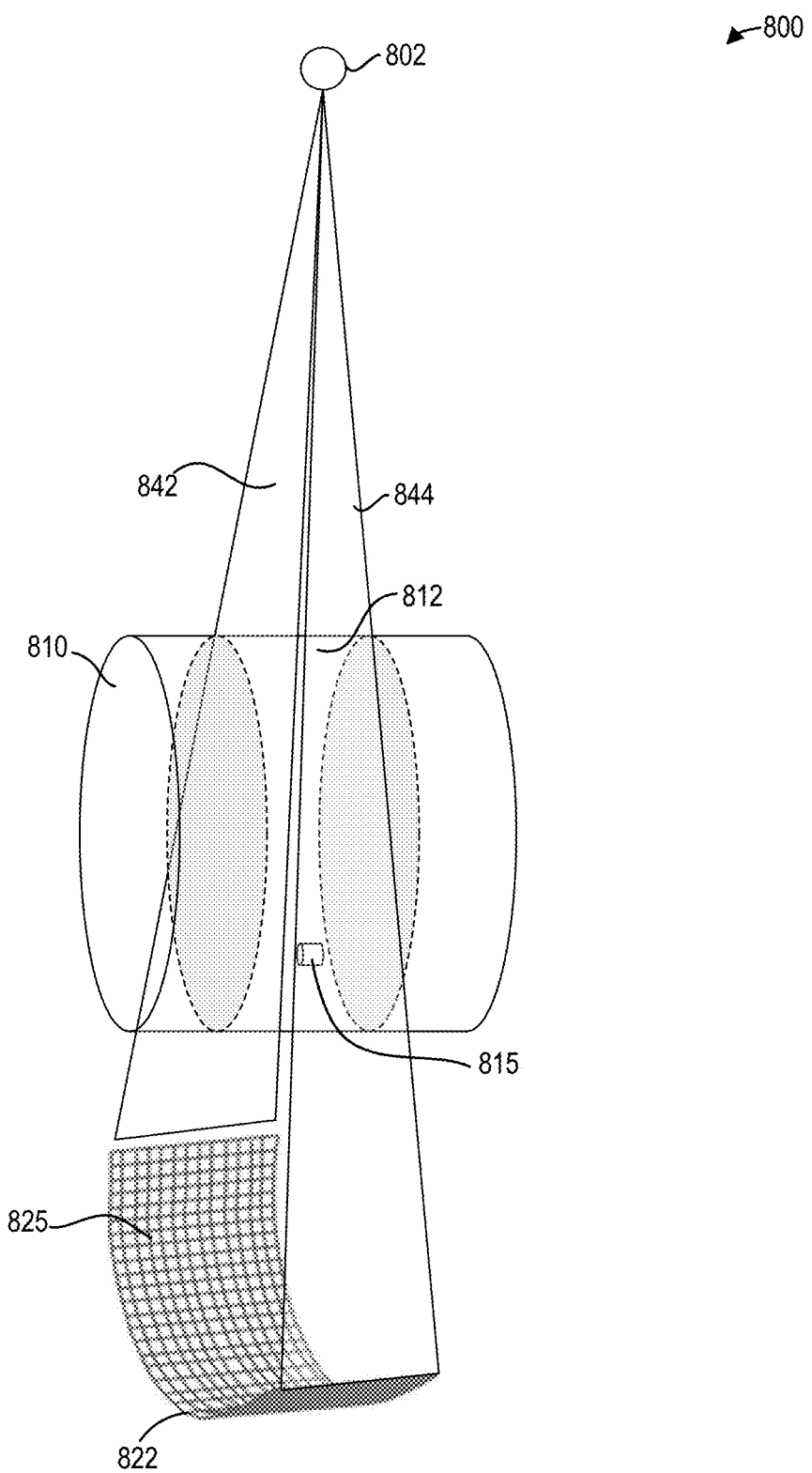
FIG. 8 shows a diagram illustrating the acquisition of projection data with a standard protocol, according to an exemplary embodiment.
Figure 9:
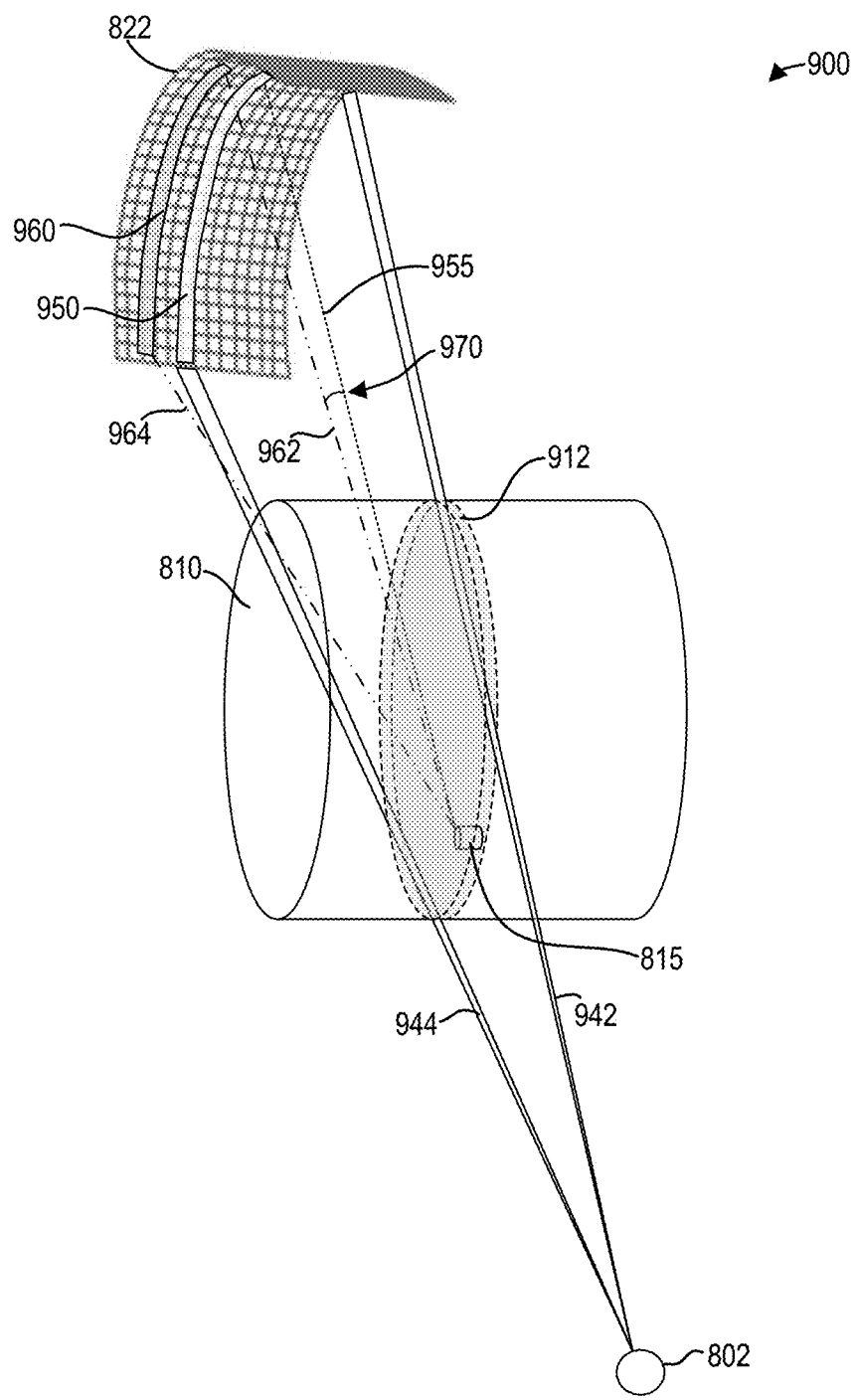
FIG. 9 shows a diagram illustrating the acquisition of coherent scatter data from a single slice, according to an exemplary embodiment.
Figure 10:
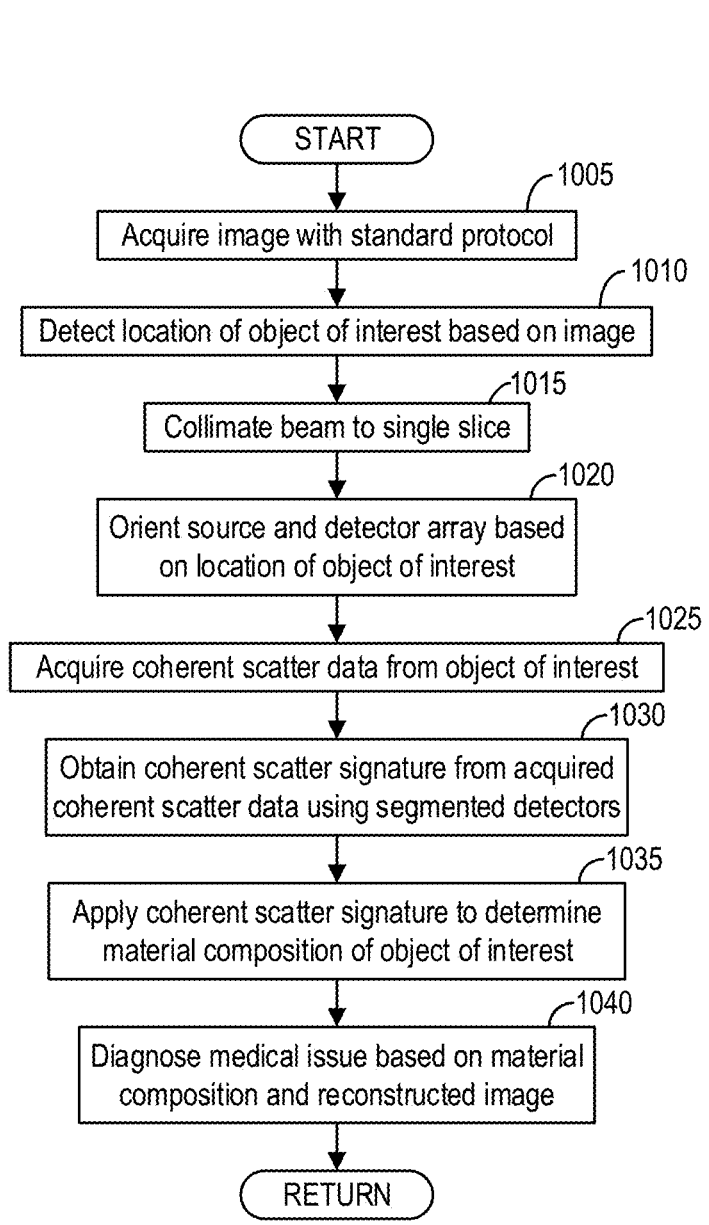
FIG. 10 shows a high-level flow chart illustrating an example method for coherent scatter CT, according to an exemplary embodiment.
Figure 11:
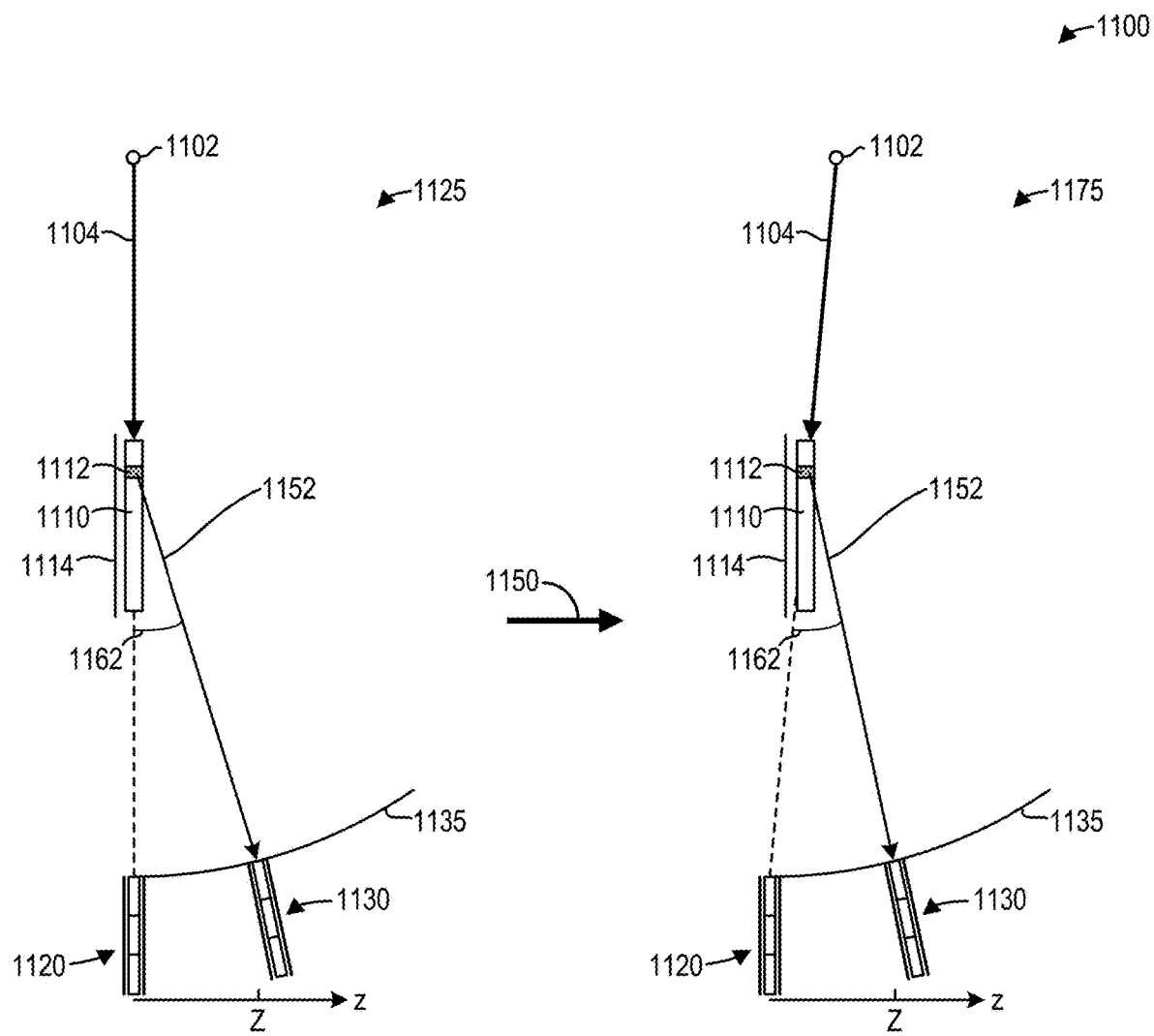
FIG. 11 shows a diagram illustrating a process for adjusting an x-ray source and a patient table to align coherent scattered rays with a segmented detector, according to an exemplary embodiment.

The following description relates to various embodiments of medical imaging systems. In particular, systems and methods are provided for coherent scatter imaging with computed tomography (CT) imaging systems. An example of a CT imaging system that may be used to acquire images in accordance with the present techniques is provided in FIGS. 1 and 2. Coherent scattering contributes to approximately ~7% of the attenuation coefficient, or amount of x-rays scattered or absorbed by the material, at clinically useful x-ray energy (e.g., percentage of coherent scattering to total mass attenuation coefficient for water at 60 keV). The coherent scatter signal shows a unique peak specific to a material at a certain photon-scattering angle. Therefore, the coherently-scattered x-rays contain valuable material-discriminating information. In conventional CT systems, the information pertaining to coherent scattered x-rays is often ignored. The primary obstacle to utilizing coherent scattered x-rays is that the receptive field of view of a detector is relatively wide, as shown in FIG. 3, and so the coherent scattered x-rays from an object of interest are difficult to ascertain due to scattered x-rays from other regions within the illuminated field of view, as shown in FIG. 4. One approach to acquiring coherent scattered x-rays from an object of interest, which may include a lesion as an illustrative and non-limiting example, includes detecting the coherent scattered x-rays with a segmented photon-counting detector, as shown in FIG. 5. The segments of a segmented photon-counting detector provide different angular sensitivity, as shown in FIG. 6, such that the receptive field of view of at least one of the segments may primarily detect coherent scattered x-rays from the object of interest, as shown in FIG. 7. Thus, a method for coherent scattered imaging may include initially acquiring an image of a volume using a standard CT protocol, as depicted in FIG. 8, and then orienting the x-ray source, detector, and patient table to illuminate a slice of the volume including the object of interest, as shown in FIG. 9. Coherent scatter data from the object of interest may then be acquired and used to determine the material composition of the object of interest, as shown in FIG. 10. In some embodiments, the x-ray source and a patient table may be adjusted in tandem such that the coherent scattered x-rays from the object of interest are optimally aligned with the segmented photon-counting detector, as shown in FIG. 11.

The CT imaging system may first acquire an image using a standard protocol so as to obtain an initial volume containing the object of interest. The CT imaging system then uses an additional protocol to characterize the object of interest in further detail. First, an x-ray source may be collimated and an orientation of a gantry may be adjusted to localize imaging of the object of interest. Further, a position of the patient table may also be adjusted to aid in localization. Then, a subsequent scan using the CT system may be conducted under conditions optimized for selective imaging of the object of interest. Angular discrimination and energy resolution afforded by a segmented x-ray detector array may be employed to capture a coherent scatter signature from the object of interest, such that individual peaks corresponding to the object of interest may be isolated. Finally, the individual peaks may be used to improve material identification of the object of interest. In this way, one or more materials of the object of interest may be determined based on the coherent scatter signature, thus aiding and improving CT-based diagnoses.

It will be appreciated by those of ordinary skill in the art that embodiments of the segmented photon-counting detectors of the present disclosure may incorporate one or more functions of phase-contrast CT imaging. In general, phase-contrast CT imaging systems utilize x-ray phase shifts to image a subject, while still measuring attenuation, electron density, and coherent scatter during imaging. The embodiments of the present disclosure may also measure attenuation, electron density, and coherent scatter, but may additionally allow CT imaging using standard protocols. Thus, two modes may be implemented: a first mode for CT imaging of a larger region of interest and a second mode for imaging an object of interest within the larger region of interest and characterizing the object of interest via received coherent scatter signals.

Figure 1:
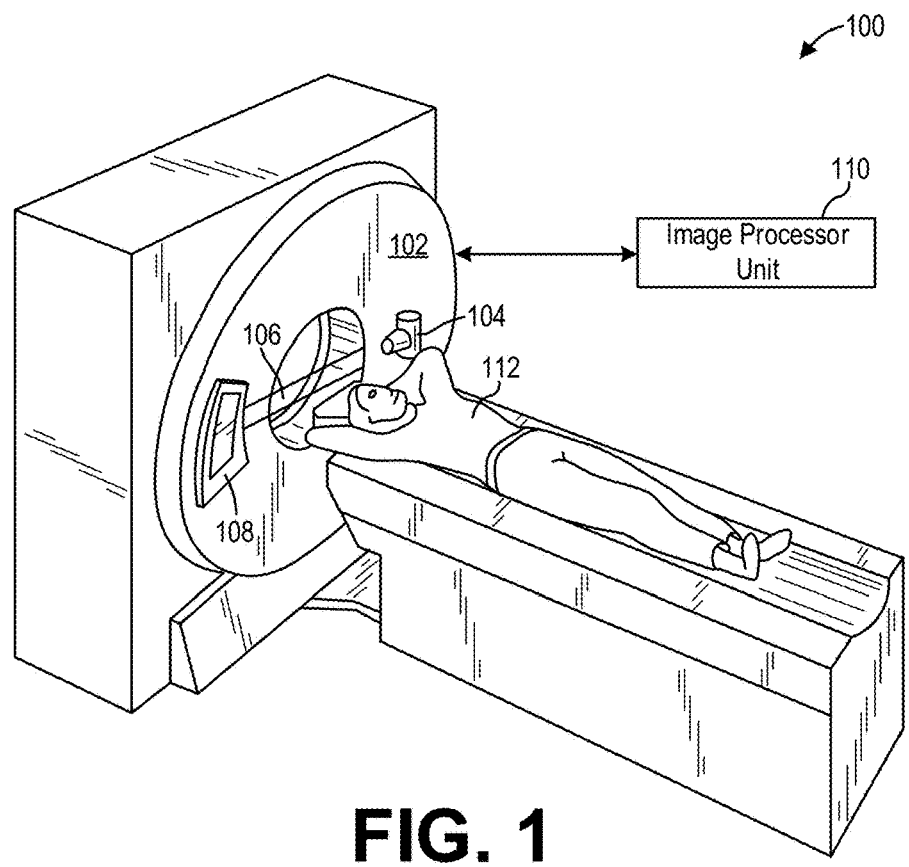
FIG. 1 shows a pictorial view of an imaging system, according to an embodiment.

FIG. 1 illustrates an exemplary CT system 100 configured for CT imaging. Particularly, the CT system 100 is configured to image a subject 112 such as a patient, an inanimate object, one or more manufactured parts, and/or foreign objects such as dental implants, stents, and/or contrast agents present within the body. In one embodiment, the CT system 100 includes a gantry 102, which in turn, may further include at least one x-ray source 104 configured to project a beam of x-ray radiation 106 for use in imaging the subject 112. Specifically, the x-ray source 104 is configured to project the x-rays 106 towards a detector array 108 positioned on the opposite side of the gantry 102. Although FIG. 1 depicts only a single x-ray source 104, in certain embodiments, multiple x-ray radiation sources and/or detectors may be employed to project a plurality of x-rays 106 for acquiring projection data at different energy levels or angular orientations corresponding to the patient. In some embodiments, the x-ray source 104 may enable dual-energy imaging by rapid peak kilovoltage (kVp) switching of the operating voltage of the x-ray tube. In some embodiments, the x-ray detector employed is a photon-counting detector which is capable of differentiating x-ray photons of different energies. In other embodiments, two sets of x-ray tube/detector pairs are used to generate dual-energy projections, with one set acquired at a low-kVp setting of the x-ray tube and the other acquired at a high-kVp setting of the x-ray tube. It should thus be appreciated that the methods described herein may be implemented with single-energy acquisition techniques as well as dual-energy acquisition techniques.

In certain embodiments, the CT system 100 further includes an image processor unit 110 configured to reconstruct images of a target volume of the subject 112 using an iterative or analytic image reconstruction method, or a combination of both. For example, the image processor unit 110 may use an analytic image reconstruction approach such as filtered backprojection (FBP) to reconstruct images of a target volume of the patient. As another example, the image processor unit 110 may use an iterative image reconstruction approach such as advanced statistical iterative reconstruction (ASIR) or model-based iterative reconstruction (MBIR), and the like, to reconstruct images of a target volume of the subject 112. As described further herein, in some examples the image processor unit 110 may use both an analytic image reconstruction approach such as FBP in addition to an iterative image reconstruction approach.

In some CT imaging system configurations, a radiation source projects a cone-shaped beam which is collimated to lie within an X-Y-Z plane of a Cartesian coordinate system and generally referred to as an "imaging volume." The radiation beam passes through an object being imaged, such as the patient or subject 112. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam intensity at the detector location, and may be used to estimate the attenuation of the beam by the object. The attenuation measurements from all the detector elements are acquired separately to produce a transmission profile.

In some CT systems, the radiation source and the detector array are rotated with a gantry about the imaging plane and around the object to be imaged such that an angle at which the radiation beam intersects the object constantly changes. A group of radiation attenuation measurements, e.g., projection data, from the detector array at one angular position of the gantry is referred to as a "view." A "scan" of the object includes a set of views made at different angular positions, or view angles, during one revolution of the radiation source and detector about the object. In some contexts, such as reduction of data acquisition time and/or applied radiation dose, a plurality of views for less than a full rotation of the gantry may be acquired, while still enabling high-fidelity image reconstruction. It is contemplated that the benefits of the methods described herein accrue to medical imaging modalities other than CT, so as used herein the term "view" is not limited to the use as described above with respect to projection data from one gantry angle. The term "view" is used to mean one data acquisition whenever there are multiple data acquisitions from different angles, whether from a CT, x-ray radiographic imaging, positron emission tomography (PET), or single-photon emission CT (SPECT) acquisition, and/or any other modality including modalities yet to be developed as well as combinations thereof in fused embodiments.

The projection data is processed to reconstruct an image that corresponds to one or more two-dimensional slices taken through the object or, in some examples where the projection data includes extended axial coverage, e.g., Z-axis illumination, a three-dimensional image volume of the object. One method for reconstructing an image from a set of projection data is referred to in the art as the filtered backprojection technique. Transmission and emission tomography reconstruction techniques also include statistical iterative methods such as maximum likelihood expectation maximization (MLEM) and ordered-subsets expectation maximization reconstruction techniques as well as iterative reconstruction techniques. This process converts the attenuation measurements from a scan into numbers called "CT numbers" or "Hounsfield units," which are used to control the brightness of a corresponding pixel on a display device.

To reduce the total scan time, a "helical" scan may be performed. To perform a "helical" scan, the patient is moved while the data for the prescribed axial coverage is acquired. Such a system generates a single helix from a cone-beam helical scan. The helix mapped out by the cone beam yields projection data from which images in each prescribed slice may be reconstructed.

As used herein, the phrase "reconstructing an image" is not intended to exclude embodiments of the present invention in which data representing an image is generated but a viewable image is not. Therefore, as used herein, the term "image" broadly refers to both viewable images and data representing a viewable image. However, many embodiments generate (or are configured to generate) at least one viewable image.

Figure 2:
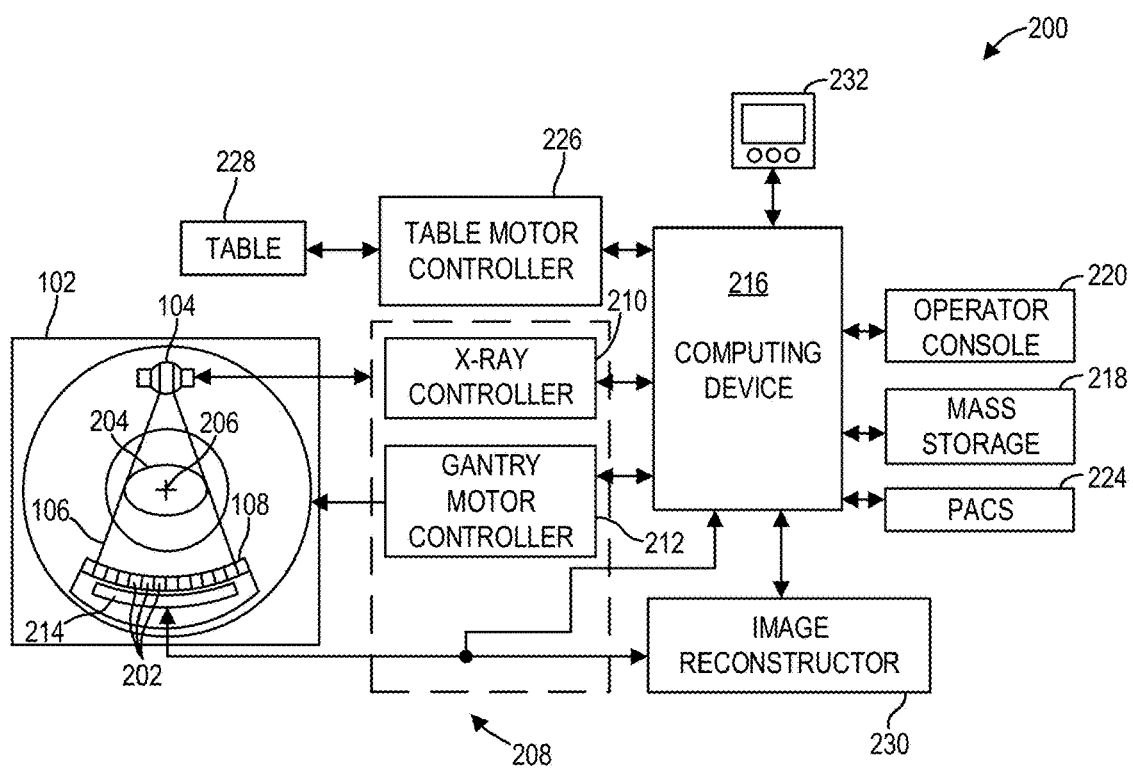
FIG. 2 shows a block schematic diagram of an exemplary imaging system, according to an embodiment.

FIG. 2 illustrates an exemplary imaging system 200 similar to the CT system 100 of FIG. 1. In accordance with aspects of the present disclosure, the imaging system 200 is configured for imaging a subject 204 (e.g., the subject 112 of FIG. 1). In one embodiment, the imaging system 200 includes the detector array 108 (see FIG. 1). The detector array 108 further includes a plurality of detector elements 202 that together sense the x-ray beams 106 (see FIG. 1) that pass through the subject 204 (such as a patient) to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle. In some industrial inspection CT systems, the x-ray source and detector may be held fixed while the object is rotated; it should be appreciated that the descriptions contained herein are also applicable to such topologies.

As the x-ray source 104 and the detector array 108 rotate, the detector array 108 collects data of the attenuated x-ray beams. The data collected by the detector array 108 undergoes pre-processing and calibration to condition the data to represent the line integrals of the attenuation coefficients of the scanned subject 204. The processed data are commonly called projections.

In some examples, the individual detectors or detector elements 202 of the detector array 108 may include photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density maps or images of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 200 reveals internal features of the subject 204, expressed in the densities of two or more basis materials. The density image, or combinations of multiple density images, may be displayed to show these features. In traditional approaches to diagnosis of medical conditions, such as disease states, and more generally of medical events, a radiologist or physician would consider a hard copy or display of one or more of the standard CT image and the density image, or combinations thereof, to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the x-ray source 104. In certain embodiments, the control mechanism 208 further includes an x-ray controller 210 configured to provide power and timing signals to the x-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The DAS 214 may reside within the control mechanism 208 or may positioned proximal to detector 108 to improve the fidelity of measurements (as shown in FIG. 2). For photon-counting imaging systems, the DAS 214 downloads measured photon counts in one or more energy bins from detector 108. The DAS 214 may be further configured to selectively aggregate analog data from a subset of the detector elements 202 into so-called macro-detectors, as described further herein. The data sampled and digitized by the DAS 214 is transmitted to a computer or computing device 216. In one example, the computing device 216 stores the data in a storage device or mass storage 218. The storage device 218, for example, may include a hard disk drive, a floppy disk drive, a compact disk read/write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 200 either includes, or is coupled to, a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 228 which may be a motorized table. Specifically, the table motor controller 226 may move the table 228 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218, either via the computing device 216 as shown in FIG. 2 or via a direct connection (not shown). Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

The various methods and processes (such as the method described below with reference to FIG. 10) described further herein may be stored as executable instructions in non-transitory memory on a computing device (or controller) in imaging system 200. In one embodiment, image reconstructor 230 may include such executable instructions in non-transitory memory, and may apply the methods described herein to reconstruct an image from scanning data. In another embodiment, computing device 216 may include the instructions in non-transitory memory, and may apply the methods described herein, at least in part, to a reconstructed image after receiving the reconstructed image from image reconstructor 230. In yet another embodiment, the methods and processes described herein may be distributed across image reconstructor 230 and computing device 216.

In one embodiment, the display 232 allows the operator to evaluate the imaged anatomy. The display 232 may also allow the operator to select a volume of interest (VOI) and/or request patient information, for example, via a graphical user interface (GUI) for a subsequent scan or processing.

As mentioned hereinabove, coherent scattering contributes to approximately ~7% of the attenuation coefficient, or amount of x-rays scattered or absorbed by the material, at clinically useful x-ray energy (e.g., percentage of coherent scattering to total mass attenuation coefficient for water at 60 keV). The coherent scatter signal shows a unique peak specific to a material at a particular scattering angle. Therefore, the coherent scattered rays contain valuable material-discriminating information. In conventional CT systems, the information pertaining to scattered coherent x-rays is often ignored.

To illustrate the difficulty in ascertaining coherent scatter information with some CT systems, FIG. 3 shows a diagram 300 illustrating coherent scatter imaging with a CT system. An x-ray source 302 emits an x-ray beam 304 towards a slice of an object 310 including an object of interest 312. The x-ray beam 304 attenuated by the object 310 is detected by the detector 322 aligned with the x-ray beam 304. Coherent scattered rays from the object 310 are detected by a detector 324 in the detector array 326, positioned at an angle 329 from a direction of the x-ray beam 304 at a position Z along a z direction as depicted. As the receptive field of view 325 of the detector 324 may be relatively wide, coherent scattered x-rays 330 from the object 310 may be detected by the detector 324, as well as coherent scattered rays 332 from the object of interest 312.

The primary obstacle to utilizing coherent scattered rays is that the receptive field of view 325 of the detector 324 is relatively wide. For example, FIG. 4 shows a graph 400 illustrating how the coherent scatter signal from an object of interest (e.g., 312) is dominated by background signals. In particular, graph 400 depicts a plot 405 of the total coherent scatter from a representative object (e.g., 310) measured by the detector 324, as well as a plot 410 of the coherent scatter from the object of interest. As shown, the coherent scatter from the object of interest is very weak in comparison to the total coherent scatter from the representative object as a whole, and so the received signal from the object of interest at the detector plane is obscured in the background scatter. Consequently, recovery of the coherent scatter from the object of interest may be exceedingly difficult.

FIGS. 3 and 4 thus illustrate that, in some cases, there may be obstacles to discriminating coherent scatter from an object of interest based upon signals collected using a non-segmented x-ray detector. One alternative approach to acquiring coherent scatter data that may be more suitable for material discrimination may include using segmented photon-counting detectors for detecting the coherent scattered x-rays. As an illustrative example, FIG. 5 shows a diagram 500 illustrating coherent scatter imaging with segmented detectors, according to an exemplary embodiment. Similar to the previous example of FIG. 3, an x-ray source 502 generates an x-ray beam 504 towards a slice of an object 510 including the object of interest 512. However, in contrast with the previous example of FIG. 3, a first detector 520 in a detector array 535 aligned with the x-ray beam 504 includes a first segment 521, a second segment 522, and a third segment 523 stacked along a direction of the x-ray beam 504, as depicted. Further, a second detector 530 in the detector array 535 also includes a first segment 531, a second segment 532, and a third segment 533 stacked along the radial direction. As such, each of the detectors 520 and 530 may be considered depth-segmented detectors, in that individual segments thereof may be stacked along a direction of incoming x-ray radiation. It should be appreciated that, while the photon-counting detectors 520 and 530 are each depicted with three segments, the detectors may be configured with a different number of segments in different examples, and that three segments per detector is provided as an illustrative and non-limiting example.

As depicted, the second detector 530 is oriented at an angle 539 relative to the direction of the x-ray beam 504 and is positioned at a distance Z from the first detector 520 along a z direction. Thus, coherent scattered rays 550 from the object 510 are incident at the detector 530.

However, the receptive field of views of the segments of the second detector 530 are different. In particular, the first segment 531 has a first receptive field of view 541, the second segment 532 has a second receptive field of view 542, and the third segment 533 has a third receptive field of view 543, wherein the first receptive field of view 541 is wider than the second receptive field of view 542, which is in turn wider than the third receptive field of view 543.

As such, coherent scattered rays 552 from the object of interest 512 are within the third receptive field of view 543 of the third segment 533 of the second detector 530, while the coherent scatter rays 550 from elsewhere in the object 510 are not within the third receptive field of view 543.

In some examples, the first detector 520 may further include an internal collimator 524 and the second detector 530 may further include an internal collimator 534. The internal collimators 524 and 534 may respectively refine an angular sensitivity of the individual segments of the photon-counting detectors 520 and 530.

FIG. 6 shows a graph 600 illustrating receptive fields of segments of a segmented detector, according to an exemplary embodiment. In particular, the graph 600 shows a plot 610 of the segment response for the first segment 531, corresponding to a first angle 612 defining the first receptive field of view 541; a plot 620 of the segment response for the second segment 532, corresponding to a second angle 622 defining the second receptive field of view 542; and a plot 630 of the segment response for the third segment 533, corresponding to a third angle 632 defining the third receptive field of view 543. The third angle 632 is the smallest, thereby indicating that the third receptive field of view 543 is smaller than the receptive fields of view 541 and 542. This angular sensitivity of the detector segments enables discrimination of coherent scatter signal from the region of interest, with a well-defined angular scatter component, from the wide-band background coherent scatter signal from the rest of the slice. Further methods to improve the fidelity of the measurement of the coherent scatter rays 552 from the object of interest 512 are detailed below with reference to FIG. 11.

FIG. 7 shows a graph 700 illustrating how a coherent scatter signal is detected with a segmented detector, according to an exemplary embodiment. The graph 700 shows a plot 705 of the total coherent scatter signal measured by the third segment 533 of the detector 530, as well as a plot 710 of the coherent scatter signal from the object of interest 512. As depicted, plot 705 of the total signal measured by the third segment 533 is highly correlated with the actual coherent scatter signal of the object of interest 512 depicted by plot 710, and is less corrupted by the background coherent scatter. Key characteristics, such as the ratio of the peak intensities, are well preserved in the detected signal shown by plot 710. Enhanced signal recovery is therefore feasible by incorporating signals from multiple pixels, pixel segments, energy bins within pixel segments, and projections.

In contrast, as the first segment 531 of the detector 530 has a relatively wide receptive field of view 541, the total coherent scatter signal measured by the first segment 531, depicted by a plot 715, resembles plot 405 of FIG. 4 for a non-segmented detector. The useful signal shown as plot 710 is similarly buried in the background for the first segment 531.

In general, locations of coherent scatter peaks are functions of corresponding energies of received photons. As such, the depth-segmented detector 530 may enable higher energy resolution by segmenting the coherent scatter. In this way, the angular sensitivity afforded by the depth-segmented detector 530 may effectively partition received coherent scatter signals from a scan, such that coherent scatter originating from the object of interest may be isolated and characterized.

In order to utilize the ability to more accurately resolve the coherent scatter signal from an object of interest with a segmented detector, methods are provided herein for coherent scatter imaging with a segmented detector. Initially, an image may be acquired with a standard CT protocol to detect the location of an object of interest, such as a lesion. As an illustrative example, FIG. 8 shows a diagram 800 illustrating the acquisition of projection data to generate an image of an object 810 with a standard protocol, according to an exemplary embodiment. As depicted, an x-ray source 802 generates beams of x-rays between edges 842 and 844 toward the object 810 to cover the detecting surface 825 of an x-ray detector array 822 including a plurality of segmented detectors. The extent of the beams of x-rays (e.g., 842, 844) correspond to wide beams aligned with the ends of the detector 822, as depicted, in accordance with a standard imaging protocol. It should be appreciated that x-rays are generated by the x-ray source 802 between the two edges 842 and 844 to image an entire volume 812 of the object 810. As depicted, the volume 812 being imaged includes an object of interest 815.

The resulting image of the volume 812 reconstructed from the detector array 822 therefore includes the object of interest 815. The particular position of the object of interest 815 within the object 810 may therefore be determined based on the images.

To perform coherent scatter imaging of the object of interest 815, the position of the x-ray source 802 and the x-ray detector array 822 may be adjusted relative to the position of the object of interest 815. As an illustrative example, FIG. 9 shows a diagram 900 illustrating the acquisition of coherent scatter data from a single slice 912, according to an exemplary embodiment. The x-ray source 802 is now collimated such that the primary x-ray beams depicted by extents 942 and 944 are directed to a single slice 912 of the object 810 that includes the object of interest 815, as depicted. In some examples, the x-ray source 802 may be collimated such that the single slice 912 is as narrow as possible. For example, the single slice 912 may be as narrow as a largest spatial dimension of the object of interest 815.

As depicted, primary x-rays originally emitted by the x-ray source 802 and attenuated within the slice 912 of the object 810 are detected by a primary subset of segmented detectors 950 in the detector array 822. For example, an x-ray 955 emitted by the x-ray source 802 and attenuated by the object of interest 815 is detected within the primary subset of segmented detectors 950.

Furthermore, coherent scattered rays 962 and 964 from the object of interest 815 are detected within a secondary subset of segmented detectors 960 in the detector array 822. A coherent scatter angle 970 between the primary x-ray 955 and the coherent scatter x-rays 962 and 964 may be dependent on the material composition of the object of interest 815, as well as the x-ray energy. Thus, by evaluating the coherent scatter acquired by particular segments of the segmented detectors within the secondary subset of segmented detectors 960, the material composition of the object of interest 815 may be determined. As noted in FIG. 7, the coherent scatter signal varies as a function of z position. As such, the expected coherent scatter signal will guide the choice of segmented detectors 960 that are used to measure the coherent scatter signal from object 815.

FIG. 10 shows a high-level flow chart illustrating an example method 1000 for coherent scatter imaging in a CT system, according to an exemplary embodiment. Method 1000 may be implemented with the imaging systems of FIGS. 1 and 2, for example, configured with segmented photon-counting detectors, as described with regard to FIG. 5. As one example, method 1000 may be implemented in non-transitory memory of a computing device, such as the computing device 216 of the imaging system 200 in FIG. 2.

Method 1000 begins at 1005. At 1005, method 1000 may include acquiring one or more initial images with a standard CT protocol. For example, method 1000 may include controlling an x-ray source to generate a beam of x-rays that illuminates an entire x-ray detector array, as depicted in FIG. 8, to thereby image a volume of a subject or object being imaged (e.g., via processing transmission profiles generated from a plurality of attenuation measurements). At 1010, method 1000 may include detecting the location of an object of interest based on the one or more initial images. For example, an object of interest such as the object of interest 815 within the volume 812 may be automatically detected or manually indicated by a user. The position of the object of interest within the imaged volume may be determined or measured or estimated.

Continuing at 1015, method 1000 may include collimating the beam of the x-ray source to a single slice, and at 1020, method 1000 may include orienting the x-ray source and the detector array based on the location of the object of interest measured at 1010. For example, method 1000 may include controlling the gantry to rotate such that the detector array is oriented to optimally capture coherent scatter from the object of interest, as depicted in FIG. 9.

Specifically, when the location of the object of interest is near an edge of the initially-imaged volume, and the x-ray source has been collimated to the single slice containing the object of interest, the gantry may be rotated so as to bring the object of interest as close as possible to the x-ray source (thereby increasing an angle between a primary x-ray beam and the coherent scatter signal) and as far as possible from the detector array. In this way, the gantry may be oriented for maximum separation of the coherent scatter signal from the primary x-ray beam at the detector array. In examples wherein the object of interest is within a threshold distance of a center of the initially-imaged volume, orienting the x-ray source and the detector array may be considered optional (as rotating the gantry would not bring the object of interest significantly closer to the x-ray source, for example).

In other embodiments, and as described below with reference to FIG. 11, each of the x-ray source and a table on which the object of interest rests may be adjusted in tandem, such that a segment of one or more detectors within the detector array may be aligned with the coherent scatter signal. Specifically, the angle between the primary x-ray beam and the coherent scatter signal may first be estimated based on a suspected material of the object of interest (e.g., a predicted peak of the coherent scatter signal specific to the suspected material may be used to estimate the angle between the coherent scatter signal and the primary x-ray beam). Then, based on the estimated angle, the x-ray controller and the table motor controller may be instructed by the computing device to respectively adjust a position of the x-ray source and/or the patient table to align the coherent scatter signal with the segment of one or more detectors. By estimating the angle between the primary x-ray beam and the coherent scatter signal that corresponds to a given peak in the coherent scatter signal, the system is optimally aligned to enhance detection of the given peak in the coherent scatter signal.

At 1025, method 1000 may include acquiring coherent scatter data from the object of interest. More specifically, method 1000 may include acquiring the coherent scatter data with segmented detectors positioned at a distance away from the primary x-ray beam emitted by the x-ray source. At 1030, method 1000 may include obtaining a coherent scatter signature from the acquired coherent scatter data using the segmented detectors, for example based on the coherent scatter angle.

At 1035, method 1000 may include applying the coherent scatter signature to determine the material composition of the object of interest. As mentioned hereinabove, the coherent scatter signal from a particular material has a unique signature at a given x-ray energy, with well-defined sharp peaks that correspond to specific angles with respect to the incoming x-ray beam. Therefore, method 1000 may include comparing the coherent scatter signature to a database or lookup table of known coherent scatter signatures to determine the one or more materials forming the material composition of the object of interest. Further, method 1000 may include using the coherent scatter signal to improve material decomposition with dual-energy or multi-energy projection data. For example, method 1000 may include determining at least two materials forming the material composition of the object of interest respectively based on low-energy x-ray radiation and high-energy x-ray radiation of the dual-energy projection data.

At 1040, method 1000 may include diagnosing a medical issue based on each of the material composition and the location of the object of interest. For example, method 1000 may include identifying a location and one or more materials characteristic of a lesion, and subsequently characterizing the object of interest as a lesion. The lesion may then be diagnosed as such, and as benign or malignant, after which treatment may be recommended. It will be appreciated that the diagnosis of the object of interest as a lesion is provided as an illustrative and non-limiting example, and that the object of interest may be characterized as any one of a number of tissues, organs, or foreign objects within a subject. It will further be appreciated that other embodiments disclosed herein may be directed to other applications beyond medical diagnostics, such as identification of one or more components of an inanimate object, for example. Method 1000 then returns.

FIG. 11 shows a diagram 1100 of an example process for adjusting 1150 an x-ray source 1102 and a patient table 1114. A first CT scan 1125 illustrates the x-ray source 1102 aligned with a first segmented detector 1120 and a second segmented detector 1130 in a detector array 1135. Further, the patient table 1114 is shown supporting a subject 1110 (e.g., a patient) such that an x-ray beam 1104 generated by the x-ray source 1102 may interact with the subject 1110, and may then be collected by the first segmented detector 1120.

The subject 1110 may include an object of interest 1112, from which coherent scattered rays 1152 may originate upon interaction of the object of interest 1112 with the x-ray beam 1104. The coherent scattered rays 1152 may be collected by the second segmented detector 1130 in the detector array 1135 at the position Z along the z direction.

In general, detectors in a CT imaging system may be designed to be focally aligned to an x-ray focal spot position (e.g., the x-ray source 1102). However, in some examples, efficient coherent scatter signal detection may be facilitated by aligning one or more detectors (e.g., the second segmented detector 1130) to a coherent scatter source. Though each portion of the subject 1110 may result in coherent scattered rays, the user of the CT imaging system may specifically be interested in the coherent scattered rays 1152 from the object of interest 1112. Thus, it may be desirable to align the second segmented detector 1130 with the coherent scattered rays 1152 from the object of interest 1112.

Adjustment 1150 of the x-ray source 1102 and the patient table 1114—either longitudinally (e.g., into or out of the CT gantry) or in height (e.g., up and down)—in tandem may allow focal alignment of the second segmented detector 1130 to the coherent scatter source (e.g., the object of interest 1112). The initial scan 1125 (e.g., prior to the adjustment 1150) may provide information regarding a position of the object of interest 1112. Provided with a suspected material composition of the object of interest 1112, an angle 1162 between the x-ray beam 1104 and the coherent scattered rays 1152 may be estimated (e.g., from a peak of a predicted coherent scatter signature specific to the suspected material composition of the object of interest 1112). As a result, the angle 1162 and the position of the object of interest 1112 may be used to adjust 1150 the x-ray source 1102 and the patient table 1114 for a second scan 1175. In this way, improved detection of the coherent scatter signature of the object of interest 1112 may be achieved. It will further be appreciated that adjusting a position of the x-ray source may include one or more of moving a position of an x-ray tube and adjusting the position of the x-ray source within the x-ray tube.

In this way, a medical imaging system is provided which may locate and acquire coherent scattered x-rays from an object of interest. A technical effect of the acquisition of the coherent scattered x-rays is that a coherent scatter signature may be determined, from which the object of interest may be identified and characterized. Another technical effect of the disclosure includes adjusting collimation of an x-ray source to illuminate a single slice containing the object of interest based on the location of the object of interest.

In one embodiment, a method comprises imaging a region of interest with an x-ray source and a segmented photon-counting detector array, detecting a position of an object of interest in the region of interest, selectively scanning, via the x-ray source and the segmented photon-counting detector array, the object of interest, detecting a coherent scatter signal from the object of interest with the segmented photon-counting detector array, and determining a material comprising the object of interest based on the detected coherent scatter signal. In a first example of the method, selectively scanning the object of interest comprises collimating the x-ray source and adjusting one or more of a position of the x-ray source, the segmented photon-counting detector array, and the object of interest to illuminate a single slice of a volume in the region of interest containing the object of interest. In a second example of the method, optionally including the first example, adjusting the one or more of the position of the x-ray source, the segmented photon-counting detector array, and the object of interest maximizes the separation of the coherent scatter signal from a primary x-ray beam on the segmented photon-counting detector array and/or optimizes an alignment of the segmented photon-counting detector array with the coherent scatter signal from the object of interest. In a third example of the method, optionally including one or more of the first and second examples, wherein selectively scanning the object of interest comprises estimating an angle between a primary x-ray beam and the coherent scatter signal, and adjusting, based on the position of the object of interest and the estimated angle, one or more of the x-ray source and the object of interest, such that a segment of one or more detectors in the segmented photon-counting detector array is optimally aligned with the coherent scatter signal. In a fourth example of the method, optionally including one or more of the first through third examples, determining the material comprising the object of interest based on the detected coherent scatter signal comprises obtaining a coherent scatter spectral signature of the object of interest from a segment of one or more detectors of the segmented photon-counting detector array, the coherent scatter spectral signature including at least one peak specific to the material comprising the object of interest. In a fifth example of the method, optionally including one or more of the first through fourth examples, imaging the region of interest includes reconstructing a viewable image depicting the object of interest, the viewable image comprising a two-dimensional slice or a three-dimensional volume or rendering.

In another embodiment, a medical imaging system comprises an x-ray source, a segmented x-ray detector array configured to detect x-ray radiation emitted by the x-ray source and attenuated by an object of interest, and a controller communicably coupled to the segmented x-ray detector array and storing instructions in non-transitory memory, the instructions executable to receive, via the segmented x-ray detector array, one or more transmission profiles generated from the detected x-ray radiation, reconstruct one or more images from the one or more transmission profiles, at least one of the one or more reconstructed images depicting an object of interest, automatically detect the object of interest based on the one or more reconstructed images, acquire, via the segmented x-ray detector array, coherent scatter data corresponding to the object of interest, and determine a material composition of the object of interest based on the coherent scatter data. In a first example of the medical imaging system, receiving the one or more transmission profiles comprises separately determining, via detectors of the segmented x-ray detector array, attenuation measurements of the detected x-ray radiation, generating the one or more transmission profiles from the acquired attenuation measurements, and receiving, at the controller, the one or more transmission profiles from the segmented x-ray detector array. In a second example of the medical imaging system, optionally including the first example, the medical imaging system further comprises a display device communicably coupled to the controller, wherein the instructions are further executable to display the one or more reconstructed images at the display device. In a third example of the medical imaging system, optionally including one or more of the first and second examples, the x-ray radiation comprises a spectrum of x-ray radiation, the segmented x-ray detector array comprises energy-discriminating detectors configured to detect, measure, and differentiate photons within different energy ranges of the x-ray radiation, and determining the material composition of the object of interest from the coherent scatter data comprises determining a plurality of materials comprising the object of interest based on the measurements of the photons within the different energy ranges of the x-ray radiation. In a fourth example of the medical imaging system, optionally including one or more of the first through third examples, determining the plurality of materials based on the measurements of the photons within the different energy ranges of the x-ray radiation comprises processing the measurements to form a plurality of material-density maps respectively corresponding to the plurality of materials, and the plurality of material-density maps are associated or combined to form a volume rendering. In a fifth example of the medical imaging system, optionally including one or more of the first through fourth examples, the segmented x-ray detector array comprises a plurality of segmented photon-counting detectors, each segmented photon-counting detector including a plurality of segments, each of the plurality of segments providing a different receptive field of view for the coherent scatter data. In a sixth example of the medical imaging system, optionally including one or more of the first through fifth examples, the plurality of segmented photon-counting detectors comprises a primary subset thereof and a secondary subset thereof, the secondary subset being configured to collect and transmit the coherent scatter data. In a seventh example of the medical imaging system, optionally including one or more of the first through sixth examples, the secondary subset is located at a distance away from the primary subset, and the receptive fields of view of the secondary subset are defined by a photon scattering angle of the x-ray radiation. In an eighth example of the medical imaging system, optionally including one or more of the first through seventh examples, the medical imaging system further comprises a gantry including the x-ray source and the segmented x-ray detector array, the segmented x-ray detector array being positioned on the gantry opposite to the x-ray source, and a gantry motor controller configured to control a rotational speed and a position of the gantry, wherein the instructions are further executable to collimate the x-ray radiation from the x-ray source to a single imaging slice containing the object of interest, and rotate the gantry via the gantry motor controller to orient the segmented x-ray detector array to capture the coherent scattering data from the object of interest.

In yet another embodiment, a method for imaging an object of interest in a subject comprises generating an image of a region of interest comprising the object of interest, determining a coherent scatter spectral signature from one or more materials of the object of interest based on x-ray radiation received at a plurality of segmented x-ray detector elements, identifying the one or more materials of the object of interest based on the coherent scatter spectral signature, and diagnosing a medical issue based on the one or more identified materials and the image. In a first example of the method, the method further comprises collecting attenuation measurements at the plurality of segmented x-ray detector elements, and wherein generating the image of the region of interest comprising the object of interest is based on the collected attenuation measurements. In a second example of the method, optionally including the first example, the method further comprises determining a position of the object of interest in the image, and based on the position of the object of interest, adjusting a collimation of an x-ray source emitting the x-ray radiation, the x-ray source disposed opposite to the plurality of segmented x-ray detector elements, and orienting one or more of the x-ray source, the plurality of segmented x-ray detector elements, and the object of interest to maximize a separation of a coherent scatter signal from a primary x-ray beam on the plurality of segmented x-ray detector elements and/or optimize an alignment of the plurality of segmented x-ray detector elements with the coherent scatter signal, the coherent scatter signal originating from the object of interest. In a third example of the method, optionally including one or more of the first and second examples, diagnosing the medical issue based on the one or more identified materials and the image comprises characterizing the object of interest as a lesion based on the one or more identified materials and a position of the object of interest in the image, and diagnosing the lesion in the subject. In a fourth example of the method, optionally including one or more of the first through third examples, identifying the one or more materials of the object of interest comprises comparing the coherent scattering spectral signature to a database or lookup table of known coherent scattering spectral signatures to identify the one or more materials.

As noted herein, given an object of interest and suspected constituent material, the angle between the primary x-ray beam and the coherent scatter x-ray signal may be determined such that the angle corresponds to a peak of the coherent scatter signal. If the photon-counting detectors have energy-discrimination capability, e.g., if the energy of the detected photons is estimated and the counted photons are partitioned among 2 or more energy bins, the spectral signature of the coherent scatter signal at a particular view angle may be estimated, where the spectral signature may refer to the energy-dependent coherent scatter signal at the chosen angular orientation (e.g., the coherent scatter signal as a function of energy). The spectral signature may further help in discriminating the material within the object of interest.

When collimating the x-ray source so that it illuminates the slice containing the object of interest, the coherent scatter generated from the object of interest may be attenuated by surrounding tissue in the object. As such, the coherent scatter signal may be attenuation. As is familiar with those skilled in the art of PET/SPECT imaging, the attenuation due to the tissue between the object of interest and the detector used to estimate the coherent scatter signal may be estimated from the original CT scan, and used to correct the amplitude of the coherent scatter signal. The correction may be applied to the total measured signal as with a photon-counting detector, or spectrally adjusted to accommodate an energy-discriminating photon-counting detector.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. Although the examples provided herein are related to medical application, the scope of the present disclosure covers non-destructive testing in industrial, biomedical, and other fields. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
    imaging a region of interest with an x-ray source and a segmented photon-counting detector array;
    detecting a position of an object of interest in the region of interest;
    selectively scanning, via the x-ray source and the segmented photon-counting detector array, the object of interest;
    detecting a coherent scatter signal from the object of interest with the segmented photon-counting detector array; and
    determining a material comprising the object of interest based on the detected coherent scatter signal.

2. The method of claim 1, wherein selectively scanning the object of interest comprises collimating the x-ray source and adjusting one or more of a position of the x-ray source, the segmented photon-counting detector array, and the object of interest to illuminate a single slice of a volume in the region of interest containing the object of interest.

3. The method of claim 2, wherein adjusting the one or more of the position of the x-ray source, the segmented photon-counting detector array, and the object of interest maximizes the separation of the coherent scatter signal from a primary x-ray beam on the segmented photon-counting detector array and/or optimizes an alignment of the segmented photon-counting detector array with the coherent scatter signal from the object of interest.

4. The method of claim 1, wherein selectively scanning the object of interest comprises:
    estimating an angle between a primary x-ray beam and the coherent scatter signal; and
    adjusting, based on the position of the object of interest and the estimated angle, one or more of the x-ray source and the object of interest, such that a segment of one or more detectors in the segmented photon-counting detector array is optimally aligned with the coherent scatter signal.

5. The method of claim 1, wherein determining the material comprising the object of interest based on the detected coherent scatter signal comprises obtaining a coherent scatter spectral signature of the object of interest from a segment of one or more detectors of the segmented photon-counting detector array, the coherent scatter spectral signature including at least one peak specific to the material comprising the object of interest.

6. The method of claim 1, wherein imaging the region of interest includes reconstructing a viewable image depicting the object of interest, the viewable image comprising a two-dimensional slice or a three-dimensional volume or rendering.

7. A medical imaging system, comprising:
    an x-ray source;
    a segmented x-ray detector array configured to detect x-ray radiation emitted by the x-ray source and attenuated by an object of interest; and
    a controller communicably coupled to the segmented x-ray detector array and storing instructions in non-transitory memory, the instructions executable to:
        receive, via the segmented x-ray detector array, one or more transmission profiles generated from the detected x-ray radiation;
        reconstruct one or more images from the one or more transmission profiles, at least one of the one or more reconstructed images depicting an object of interest;
        automatically detect the object of interest based on the one or more reconstructed images;
        acquire, via the segmented x-ray detector array, coherent scatter data corresponding to the object of interest; and
        determine a material composition of the object of interest based on the coherent scatter data.

8. The medical imaging system of claim 7, wherein receiving the one or more transmission profiles comprises:
    separately determining, via detectors of the segmented x-ray detector array, attenuation measurements of the detected x-ray radiation;
    generating the one or more transmission profiles from the acquired attenuation measurements; and
    receiving, at the controller, the one or more transmission profiles from the segmented x-ray detector array.

9. The medical imaging system of claim 7, further comprising:
    a display device communicably coupled to the controller, wherein the instructions are further executable to display the one or more reconstructed images at the display device.

10. The medical imaging system of claim 7, wherein
    the x-ray radiation comprises a spectrum of x-ray radiation,
    the segmented x-ray detector array comprises energy-discriminating detectors configured to detect, measure, and differentiate photons within different energy ranges of the x-ray radiation, and
    determining the material composition of the object of interest from the coherent scatter data comprises determining a plurality of materials comprising the object of interest based on the measurements of the photons within the different energy ranges of the x-ray radiation.

11. The medical imaging system of claim 10, wherein
    determining the plurality of materials based on the measurements of the photons within the different energy ranges of the x-ray radiation comprises processing the measurements to form a plurality of material-density maps respectively corresponding to the plurality of materials, and
    the plurality of material-density maps are associated or combined to form a volume rendering.

12. The medical imaging system of claim 7, wherein the segmented x-ray detector array comprises a plurality of segmented photon-counting detectors, each segmented photon-counting detector including a plurality of segments, each of the plurality of segments providing a different receptive field of view for the coherent scatter data.

13. The medical imaging system of claim 12, wherein the plurality of segmented photon-counting detectors comprises a primary subset thereof and a secondary subset thereof, the secondary subset being configured to collect and transmit the coherent scatter data.

14. The medical imaging system of claim 13, wherein
the secondary subset is located at a distance away from the primary subset, and
the receptive fields of view of the secondary subset are defined by a photon scattering angle of the x-ray radiation.

15. The medical imaging system of claim 7, further comprising:
a gantry including the x-ray source and the segmented x-ray detector array, the segmented x-ray detector array being positioned on the gantry opposite to the x-ray source; and
a gantry motor controller configured to control a rotational speed and a position of the gantry,
wherein the instructions are further executable to:
collimate the x-ray radiation from the x-ray source to a single imaging slice containing the object of interest; and
rotate the gantry via the gantry motor controller to orient the segmented x-ray detector array to capture the coherent scattering data from the object of interest.

16. A method for imaging an object of interest in a subject, the method comprising:
generating an image of a region of interest comprising the object of interest;
determining a coherent scatter spectral signature from one or more materials of the object of interest based on x-ray radiation received at a plurality of segmented x-ray detector elements;
identifying the one or more materials of the object of interest based on the coherent scatter spectral signature; and
diagnosing a medical issue based on the one or more identified materials and the image.

17. The method of claim 16, further comprising collecting attenuation measurements at the plurality of segmented x-ray detector elements, and
wherein generating the image of the region of interest comprising the object of interest is based on the collected attenuation measurements.

18. The method of claim 16, further comprising:
determining a position of the object of interest in the image; and
based on the position of the object of interest:
adjusting a collimation of an x-ray source emitting the x-ray radiation, the x-ray source disposed opposite to the plurality of segmented x-ray detector elements, and
orienting one or more of the x-ray source, the plurality of segmented x-ray detector elements, and the object of interest to maximize a separation of a coherent scatter signal from a primary x-ray beam on the plurality of segmented x-ray detector elements and/or optimize an alignment of the plurality of segmented x-ray detector elements with the coherent scatter signal, the coherent scatter signal originating from the object of interest.

19. The method of claim 16, wherein diagnosing the medical issue based on the one or more identified materials and the image comprises:
characterizing the object of interest as a lesion based on the one or more identified materials and a position of the object of interest in the image; and
diagnosing the lesion in the subject.

20. The method of claim 16, wherein identifying the one or more materials of the object of interest comprises comparing the coherent scattering spectral signature to a database or lookup table of known coherent scattering spectral signatures to identify the one or more materials.

* * * * *